United States Patent [19]

Yadan et al.

[11] Patent Number: 5,438,151
[45] Date of Patent: Aug. 1, 1995

[54] PROCESS FOR THE PREPARATION OF ERGOTHIONEINE

[75] Inventors: Jean C. Y. Yadan, Paris; Jinzhu Xu, Ivry sur Seine, both of France

[73] Assignee: Bioxytech, Bonneuil-Sur-Marne, France

[21] Appl. No.: 194,457

[22] Filed: Feb. 8, 1994

[30] Foreign Application Priority Data

Jun. 28, 1993 [FR] France .................................. 93 07839
Dec. 22, 1993 [FR] France .................................. 93 15457

[51] Int. Cl.$^6$ ............................................ C07D 233/64
[52] U.S. Cl. .................................................. 548/324.1
[58] Field of Search ...................................... 548/324.1

[56] References Cited

PUBLICATIONS

H. Heath et al J.C.S. (London), 1951, pp. 2215–2217.

*Primary Examiner*—David B. Springer
*Attorney, Agent, or Firm*—Jacobson, Price, Holman & Stern

[57] ABSTRACT

The invention relates to a novel process for the preparation of ergothioneine.

The process for the chemical synthesis of the different optical forms of ergothioneine essentially comprises steps which consist in preparing or using an $N_\alpha,N_\alpha$-dimethylated histidine ester salt (optically active if necessary), treating this compound with an alkyl, alkenyl or aryl halogenothionoformate in the presence of a base, protecting the sulfur-containing substituent in the compound obtained, converting this protected compound to a compound of the trimethylammonium type and freeing the desired ergothioneine by saponification or acid hydrolysis, as appropriate.

This process affords a better yield and ensures an excellent optical purity.

28 Claims, No Drawings

PROCESS FOR THE PREPARATION OF ERGOTHIONEINE

The present invention relates to a novel process for the preparation of the different optical forms of ergothioneine, in particular D,L-ergothioneine and L-(+)-ergothioneine, which is a natural molecule.

I/STATE OF THE ART

L-Ergothioneine or 2-mercapto-$N_\alpha,N_\alpha,N_\alpha$-trimethyl-L-histidine is a natural molecule which was isolated from the rye ergot fungus *Claviceps purpurea* (see the communication by Tanret C., C.R. Acad. Sci., 149, (1909), pages 222–224). It was subsequently identified in rat erythrocytes and liver and then in numerous other animal tissues, in particular in man (see the article by Melville D. B. in Vitam. Horm., 17, (1958), pages 155–204). It is biosynthesized exclusively by fungi and mycobacteria. In plants, ergothioneine is assimilated by the roots after fungal synthesis inside the conidia. In man, it is assimilated solely through food.

Although the exact biological role of ergothioneine is still uncertain, its antioxidizing properties are well documented (see the article by Hartman P.E. in Meth. Enzymol., 186, (1990), pages 310–318, and the article by Akanmu D. et al. in the journal Arch. Biochem. Biophys., 288, (1991), pages 10–16). Ergothioneine can thus be used as a food additive or in cosmetics, or even in medicine, by virtue of its antioxidizing properties.

Ergothioneine has been obtained either by a microbiological route (see the document JP-A-43-020 716 (1968) in the name of Miyoshi T. and Sakai H.) or by a chemical route (see the article by Heath H. et al. in the journal J. Chem. Soc., pages 2215–17, (1951), and the article by Sunko D. E. and Wolf G. in the journal *J. Chem. Soc.*, pages 4405–4406, (1958)). For the latter route to be practicable, it is necessary to overcome the following three difficulties:

* the very ready $\beta$-elimination of the trimethylammonium group, in an alkaline medium, to give 2-mercaptourocanic acid;
* the methylation of a nitrogen-containing group in the presence of a sulfur-containing group; and
* the very easy racemization of ergothioneine, in a weakly alkaline medium, because of its betaine-type structure.

Furthermore, to prepare this compound on the industrial scale, it is necessary to have an overall yield greater than or equal to at least 20%.

The key intermediate in the synthetic preparations of the prior art is 2-mercaptohistidine, which is obtained either by degradation of the imidazole ring of the histidine, followed by synthesis of the 2-mercaptoimidazole ring with the aid of potassium thiocyanate (see Heath's article cited above), or by total synthesis (see Sunko's article cited above as well as the article by Hegedus B. in the journal Helv. Chim. Acta, 38, (1955), pages 22–27).

The preparation of ergothioneine from 2-mercaptohistidine then always uses the same process (see Heath's article cited above), which represents the main snag in these preparations. In fact, the final methylation step necessitates the use of large amounts of silver oxide, hydrogen sulfide to remove the silver salts, and then phosphotungstic acid, all under particularly harsh conditions. Furthermore, this last step is laborious to carry out and appears to be inapplicable to the preparation of ergothioneine on the industrial scale. Finally, the ergothioneine obtained is partially or even totally racemized and the poor overall yield of these preparations never exceeds 9%.

In view of the well-known interest, resulting from the documents cited above, which has been created by ergothioneine in general and L-(+)-ergothioneine in particular, the Applicant sought a novel synthesis of these molecules which would make it possible to avoid the above-mentioned disadvantages while at the same time giving the desired product under very mild conditions, with a good overall yield and with an excellent optical purity, preferably in excess of 98%.

This object is achieved according to the invention, which provides a novel synthesis of ergothioneine based on a novel process for the synthesis of the 2-mercaptoimidazole ring.

The key step in the process according to the invention is based on a novel strategy whereby the sulfur atom is introduced into the imidazole ring by means of a reaction whose mechanism has something in common with a mechanism of the type "Nucleophilic Addition—Ring Opening—Ring Closure" (NAORC).

More precisely, the invention relates to a process for the chemical synthesis of the different optical forms of ergothioneine, in particular the (D,L) and (L) forms, which essentially comprises steps consisting in:

a) preparing or using an $N_\alpha,N_\alpha$-dimethylated histidine ester salt (optically active if necessary);
b) treating this compound with an alkyl, alkenyl or aryl halogenothionoformate, in particular a phenyl halogenothionoformate, in the presence of a base;
c) protecting the sulfur-containing substituent in the compound obtained and converting this protected compound to a compound of the trimethylammonium type; and
d) freeing the desired ergothioneine by saponification or acid hydrolysis, as appropriate.

The histidine ester is advantageously a $C_1$-$C_6$-alkyl ester, especially a methyl ester.

The salt is advantageously a halide, especially a dihydrochloride.

The starting material can be a commercial compound such as the dihydrochloride of L-histidine methyl ester, which is methylated.

The starting material can also be a salt of $N_\alpha,N_\alpha$-dimethyl-L-histidine methyl ester, obtained by the process of Reinhold V. N. et al. described in the journal *J. Med. Chem.*, 11, (1968), pages 258–260.

The aryl halogenothionoformate used is advantageously phenyl chlorothionoformate.

The base used during the treatment with this last compound is for example sodium bicarbonate or an amine or alkylamine, in particular triethylamine.

The sulfur-containing substituent can be protected by acylation, preferably by means of a halogenoformate which is conventionally used in this case, for example an ethyl or phenyl halogenoformate, in particular the chloroformate.

The conversion to the compound of the trimethylammonium type is effected by means of an alkylating agent such as a methyl halide, in particular methyl iodide, or dimethyl sulfate.

This last compound is saponified for example by means of an amine, in particular an alkylamine and preferably triethylamine, in a water/alcohol mixture. A currently preferred alcohol is methanol.

In one variant, especially in the case where the starting material is an optically active compound so as to give an ergothioneine which is also optically active, the above compound of the trimethylammonium type is advantageously hydrolyzed by means of an acid solution, for example a concentrated solution of hydrochloric acid, preferably in the presence of a large excess of a mercaptan. The mercaptan used is advantageously an alkyl- or aryl-mercaptan, preferably β-mercaptopropionic acid.

In one particular embodiment, the invention relates to a process for the chemical synthesis of D,L-ergothioneine which essentially comprises steps consisting in:

a) preparing or using an $N_\alpha,N_\alpha$-dimethylated histidine ester salt;

b) treating this compound with an alkyl, alkenyl or aryl halogenothionoformate, in particular a phenyl halogenothionoformate, in the presence of a base;

c) protecting the sulfur-containing substituent in the compound obtained, preferably by acylation and particularly preferably by means of an alkyl or phenyl halogenoformate, in the presence of a base, preferably triethylamine;

d) treating the protected compound obtained with an alkylating agent, preferably a methyl halide in an alcohol; and e) freeing the desired D,L-ergothioneine by saponification, preferably by means of an amine in a water-/alcohol mixture.

In one preferred embodiment, the invention relates to a process for the chemical synthesis of L-(+)-ergothioneine which essentially comprises steps consisting in:

a) preparing or using an $N_\alpha,N_\alpha$-dimethylated histidine ester salt;

b) treating this compound with an alkyl, alkenyl or aryl halogenothionoformate, in particular a phenyl halogenothionoformate, in the presence of a base;

c) protecting the sulfur-containing substituent in the compound obtained, preferably by acylation and particularly preferably by means of an alkyl or phenyl halogenoformate, in the presence of a base, preferably triethylamine;

d) treating the protected compound obtained with an alkylating agent, preferably a methyl halide in an alcohol; and e) freeing the desired L-(+)-ergothioneine by acid hydrolysis, preferably by means of a solution of strong acid.

In one advantageous embodiment, the abovementioned methyl halide is methyl iodide and the abovementioned alcohol is methanol.

In one preferred embodiment, the acid hydrolysis for freeing the L-(+)-ergothioneine is carried out in the presence of a large excess of a mercaptan. The mercaptan used will advantageously be an alkyl- or aryl-mercaptan. A particularly preferred mercaptan at the present time is β-mercaptopropionic acid. The above-mentioned strong acid is advantageously a concentrated solution of hydrochloric acid.

Advantageously, the mercaptan is present in a molar ratio of at least 50, preferably at least 70, relative to the ester. It should be noted that the function of the mercaptan is to trap the carbocation generated during the acid hydrolysis, so as to avoid any spurious reaction with the sulfur atom in the 2-mercaptoimidazole ring.

The reaction atmosphere is not critical but, for practical reasons, the Examples below were carried out under an inert nitrogen atmosphere.

In one or other of the foregoing features of the invention, the treatment of the compound with an alkyl, alkenyl or aryl halogenothionoformate can be carried out in the presence of a base in a polar solvent. This base can be selected from a bicarbonate, an amine or an alkylamine, in particular diethylamine or triethylamine.

In one preferred embodiment for obtaining a better yield, this treatment is carried out in two steps. A first step consists in carrying out the reaction in an aqueous solution of a weak base, preferably one with a pKa of less than about 9, in particular a bicarbonate, advantageously in the presence of a polar solvent favoring the solubility of the chlorothionoformate, for example ethyl ether. This reaction is advantageously performed by the dropwise addition of a solution of the halogenothionoformate in the polar solvent, at room temperature, to said solution containing the compound to be treated in the aqueous solution of bicarbonate. The intermediate containing the opened imidazole ring is recovered from the organic phase of the solvent, for example ethyl ether, advantageously dried, for example over $MgSO_4$, to remove the residual water, and evaporated to give an oil. This oil is then treated with another base, preferably one with a pKa of more than about 10 and particularly preferably an organic base, advantageously of the amine or alkylamine type, in particular diethylamine or triethylamine, for several hours at room temperature, advantageously in the presence of a polar solvent. Preferably, this polar solvent is an ether, in particular tetrahydrofuran. The solvent is then removed to give the desired reaction product.

It should be noted that the first step is particularly difficult because there is a very high risk of racemization of the optically active starting compound. It has been possible to observe that this risk of racemization is particularly high in the presence of a strong base. Thus the first step has to be carried out in the presence of a weak base, bicarbonate being particularly suitable for this reaction. In addition, the overall yield of formation of the imidazole ring is particularly high, i.e. above 70%, compared with a yield of the order of 40% obtained by a one-step procedure.

Furthermore, each of the D and L optical isomers of ergothioneine can be obtained from the racemic (D,L)-ergothioneine by analogy with the known techniques for resolving amino acids.

Other objects, characteristics and advantages of the invention will become clearly apparent from the following explanatory description referring to various Examples of the invention, which are given simply by way of illustration and cannot in any way limit the scope of the invention. All the percentages are given by weight in the Examples, unless indicated otherwise.

In the Examples, all the reactions were performed under an inert nitrogen atmosphere, unless indicated otherwise.

The mass spectra were run on a Nermag R10-10B instrument. The ionization mode used is either electron impact (EI) at 70 electron-volts, or chemical ionization (CI) in ammonia, or fast atom bombardment (FAB) on a glycerol matrix.

The $^1H$ and $^{13}C$ NMR spectra were run on a Varian Gemini-200 instrument. The chemical shifts are expressed in ppm relative to tetramethylsilane. The multiplicities are expressed as follows: "s" for singlet, "bs" for broad singlet, "d" for doublet, "t" for triplet, "q" for quadruplet and "m" for multiplet.

The melting points (m.p. ° C.) were recorded on a Gallenkamp instrument and are given uncorrected.

The optical rotation ($\alpha_D$) was measured on a Perkin Elmer 241 instrument at 25° C. on the sodium D line.

The purifications by column liquid chromatography were effected with Merck® Si60 F$_{254}$ silica or Merck® microcrystalline cellulose, as appropriate.

EXAMPLE 1: Preparation of D,L-ergothioneine:

A - Preparation of the dihydrochloride of L-(+)-N$_\alpha$,N$_\alpha$-dimethylhistidine methyl ester:

A 37% aqueous solution of formaldehyde (Janssen; 12.29 g; 150 mmol) is added to a solution of the dihydrochloride of L-(+)-histidine methyl ester (Janssen; 18.16 g; 75 mmol) in 150 ml of deionized water. The mixture is hydrogenated under pressure (7 b) in the presence of 10% palladium-on-charcoal (Aldrich; 1.0 g) for 5 h at room temperature. The catalyst is filtered off and then rinsed with water; the filtrate is evaporated to dryness under vacuum to give the expected product in the form of an oil (20.3 g), which is used directly in the next step.

Physical characteristics:

$^1$H NMR (200 MHz, D$_2$O):

2.91 ppm (s; 6H); 3.50 ppm (m; 2H); 3.72 ppm (s; 3H); 4.48 ppm (dd; J=5.54–9.04 Hz; 1H); 7.38 ppm (s; 1H); 8.61 ppm (s; 1H).

B - Preparation of (D,L)-2'-mercapto-N$_\alpha$N$_\alpha$-dimethylhistidine methyl ester:

The dihydrochloride of N$_\alpha$,N$_\alpha$-dimethylhistidine methyl ester (27.0 g; 100 mmol) is dissolved in 450 ml of water. Sodium bicarbonate (Labosi; 58.8 g; 700 mmol) is added slowly, followed by 450 ml of THF. Phenyl chlorothionoformate (Lancaster; 34.5 ml; 250 mmol) is added dropwise to this mixture over 30 min, with stirring. The reaction mixture is stirred for 24 h at 80° C. The two-phase mixture is then decanted. The two phases are separated and the organic phase is dried. The solvent is evaporated off under vacuum. The residue of the organic phase is chromatographed on SiO$_2$ (eluent: AcOEt) to give 12.02 g of the expected ester. Yield of 2'-mercapto-N$_\alpha$,N$_\alpha$-dimethylhistidine methyl ester: 52%.

Physical characteristics:

* m.p.: 171°–173° C.

* $^1$H NMR (200 MHz, CDCl$_3$):

2.39 ppm (s; 6H); 2.78 ppm (d; J=7.30 Hz; 2H); 3.38 ppm (t; J=7.30 Hz; 1H); 3.72 ppm (s; 3H); 6.44 ppm (s; 1H); 10.08 ppm (bs; 1H); 10.24 ppm (bs; 1H).

* $^{13}$C NMR (50 MHz, DMSO-d$_6$):

24.52 ppm (t); 41.03 ppm (q); 51.03 ppm (d); 65.04 ppm (q); 112.74 ppm (d); 126.13 ppm (s); 160.35 ppm (s); 171.17 ppm (s).

* MS (EI, 70 eV):

229 (M+; 25); 170 (8); 116 (100).

C - Preparation of (D,L)-1'-ethoxycarbonyl-2'-ethoxycarbonythio-N$_{60}$N$_\alpha$-dimethylhistidine methyl ester:

2'-Mercapto-N$_\alpha$,N$_\alpha$-dimethylhistidine methyl ester (12.80 g; 55.9 mmol) is dissolved in 200 ml of dichloromethane under an inert atmosphere. Triethylamine (Janssen; 23.3 ml; 168 mmol) is added. Ethyl chloroformate (Janssen; 12.8 ml; 134 mmol) is then added dropwise at 0° C. over 30 min. The reaction mixture is stirred for 1 h at room temperature and then hydrolyzed by the addition of 150 ml of a saturated aqueous solution of NaCl. The organic phase is decanted and then washed with the same volume of a saturated aqueous solution of NaCl, dried over MgSO$_4$ and evaporated to dryness under vacuum. The crude product is purified by chromatography on a silica column (eluent: AcOEt/cyclohexane 1/1) to give 18.71 g of the desired product (yield: 90%).

Physical characteristics:

* $^1$H NMR (200 MHz, CDCl$_3$):

1.25 ppm (t; J=7.16 Hz; 3H); 1.35 ppm (t; J=7.16 Hz; 3H); 2.31 ppm (s; 6H); 2.81 ppm (dd; J=6.54–14.66 Hz; 1H); 2.96 ppm (dd; J=8.46–14.66 Hz; 1H); 3.60 ppm (dd; J=6.54–8.46 Hz; 1H); 3.62 ppm (s; 3H); 4.26 ppm (q; J=7.16 Hz; 2H); 4.36 ppm (q; J=7.16 Hz; 2H); 7.41 ppm (s; 1H).

* $^{13}$C NMR (50 MHz, CDCl$_3$):

172.41 ppm (s); 167.40 ppm (s); 148.55 ppm (s); 140.76 ppm (s); 135.12 ppm (s); 120.15 ppm (d); 66.89 ppm (q); 65.17 ppm (t); 64.88 ppm (t); 51.51 ppm (d); 41.99 ppm (q); 27.97 ppm (t); 14.37 ppm (q); 14.18 ppm (q).

* MS (EI, 70 eV):

373 ((M+; 6); 314 (26); 116 (100).

D - Preparation of (D,L]-1'-ethoxycarbonyl-2'-ethoxycarbonylthio-N$_\alpha$,-N$_\alpha$,N$_\alpha$-trimethylhistidine methyl ester:

Iodomethane (Lancaster; 0.6 ml; 9.6 mmol) is added to a solution of (D,L)-1'-ethoxycarbonyl-2'-ethoxycarbonylthio-N$_{60}$,N$_\alpha$-dimethylhistidine methyl ester (0.64 g; 1.72 mmol) in 20 ml of methanol. The mixture is stirred at room temperature under nitrogen for 70 h. The solvent and the excess iodomethane are evaporated off under vacuum at room temperature to give an oil, which contains essentially the expected ammonium compound and is used as such for the next step.

Physical characteristics:

* $^1$H NMR (200 MHz, acetone-d$_6$):

1.26 ppm (t; J=7.16 Hz; 3H); 1.37 ppm (t; J=7.16 Hz; 3H); 3.50–3.60 ppm (m; 2H); 3.64 ppm (s; 9H); 3.74 ppm (s; 3H); 4.33 ppm (q; J=7.16 Hz; 2H); 4.44 ppm (q; J=7.16 Hz; 2H); 4.84 ppm (dd; J=4.08–10.84 Hz; 1H); 7.99 ppm (s; 1H).

E - Preparation of D,L-ergothioneine:

1'-Ethoxycarbonyl-2'-ethoxycarbonylthio-N$_{60}$,N$_\alpha$,-N$_\alpha$-trimethylhistidine methyl ester (0.85 g; 1.65 mmol) is dissolved in 25 ml of triethylamine/water/methanol (1:4:6). The solution is heated at 60° C. for 45 h. The solvents are evaporated off to dryness under vacuum to give a solid residue. This is purified by chromatography on a cellulose column (eluent: MeOH/H$_2$O 9/1) to give D,L-ergothioneine (0.35 g; 89%).

Physical characteristics:

* m.p.: 275° C. (dec.); recrystallized from EtOH/H$_2$O=1:1.

* $^1$H NMR (200 MHz, D$_2$O):

3.01–3.18 ppm (s; 9H superimposed on m; 2H); 3.80 ppm (dd; J=4.52–11.24 Hz; 1H); 6.70 ppm (s; 1H).

* $^{13}$C NMR (50 MHz, D$_2$O):

173.11 ppm (s); 158.82 ppm (s); 126.68 ppm (s); 118.11 ppm (d); 79.82 ppm (d); 54.79 ppm (q); 25.38 ppm (t).

These NMR spectra are identical to those obtained from a commercial sample of ergothioneine (ICN, France).

* UV (H$_2$O, c=36.7 μM): $\lambda_{max}$=257 nm. This value is consistent with the information given in the Merck Index, 11th ed. (1989).

The overall preparative yield of the D,L-ergothioneine obtained by this procedure is 41%.

EXAMPLE 2: Preparation of L-(+)-ergothioneine:

A - Preparation of L-(+)-2'-mercapto-$N_\alpha,N_\alpha$-dimethylhistidine methyl ester:

The dihydrochloride of L-(+)-$N_\alpha,N_\alpha$-dimethylhistidine methyl ester (60.0 g; 222 mmol) is dissolved in 750 ml of deionized water. Solid sodium bicarbonate (Labosi; 130.5 g; 1.55 mol) is added slowly, followed by 750 ml of THF. Phenyl chlorothionoformate (Lancaster; 76 ml; 555 mmol) is added over 30 min at a temperature between 5 and 10° C., with vigorous stirring. The reaction mixture is stirred at room temperature for 260 h. The aqueous phase is decanted and then extracted with methylene chloride (3×150 ml). The organic phases are combined and then evaporated to dryness under vacuum at room temperature. The residue is then purified by chromatography on a silica column using an elution gradient (AcOEt-AcOEt/MeOH=100%-95/5) to give 24.0 g of a pure product. This product (5.0 g) is suspended in 150 ml of methylene chloride and the suspension is then filtered. The residue obtained after evaporation of the solvent from the filtrate gives 4.42 g of an enantiomerically pure product (yield: 42%).

The enantiomeric purity is determined by $^1$H NMR in CDCl$_3$ with 3 mg of sample and 10 mg of Eu(tfc)$_3$.

Physical characteristics:
* m.p.: 170°-171° C.
* $^1$H NMR (200 MHz, CDCl$_3$):
2.39 ppm (s; 6H); 2.78 ppm (d; J=7.3 Hz; 2H); 3.38 ppm (t; J=7.30 Hz; 1H); 3.72 ppm (s; 3H); 6.44 ppm (s; 1H); 10.08 ppm (bs; 1H); 10.24 ppm (bs; 1H).
* $^{13}$C NMR (50 MHz, DMSO):
24.52 ppm (t); 41.03 ppm (q); 51.03 ppm (d); 65.04 ppm (q); 112.74 ppm (d); 126.13 ppm (s); 160.35 ppm (s); 171.17 ppm (s).
* MS (EI, 70 eV):
229 (M+; 25); 170 (8); 116 (100).
* $\alpha_D$ (c=1.0; MeOH)=+31.2°.

B - Preparation of L-(+)-1'-ethoxycarbonyl-2'-ethoxy-carbonylthio-$N_{60},N_\alpha$-dimethylhistidine methyl ester:

Triethylamine (Janssen; 5.85 ml; 42.0 mmol) is added to a solution of the above compound (3.85 g; 16.8 mmol) in 80 ml of methylene chloride, cooled to 10° C. Ethyl chloroformate (Janssen; 3.5 ml; 37.0 mmol) is added dropwise at this temperature. When the addition has ended, a precipitate of triethylamine hydrochloride appears. The reaction mixture is stirred for 0.5 h at 10° C. and the excess ethyl chloroformate is then hydrolyzed by the addition of 50 ml of water. The organic phase is decanted, washed with water (2×50 ml) and finally dried over MgSO$_4$. Evaporation of the solvent under reduced pressure gives 6.19 g of a very slightly yellow oil, which is used as such in the next step (yield: 99%).

Physical characteristics:
* $^1$H NMR (200 MHz, CDCl$_3$):
1.28 ppm (t; J=7.16 Hz; 3H); 1.40 ppm (t; J=7.16 Hz; 3H); 2.33 ppm (s; 6H); 2.83 ppm (dd; J=6.50-14.60 Hz; 1H); 2.98 ppm (dd; J=8.50-14.60 Hz; 1H); 3.65 ppm (dd; J=6.50-8.50 Hz; 1H); 3.68 ppm (s; 3H); 4.28 ppm (q; J=7.16 Hz; 2H); 4.42 ppm (q; J=7.16 Hz; 2H); 7.44 ppm (s; 1H).
* MS (EI, 70 eV):
373 (M+; 9); 314 (29); 116 (100).
* $\alpha_D$ (c=1.1; CH$_2$Cl$_2$)=−5.8°.

C - Preparation of L-+)-1'-ethoxycarbonyl-2'-ethoxycarbonylthio-$N_\alpha,N_\alpha,N_\alpha$-trimethylhistidine methyl ester:

The product of the previous step (6.19 g; 16.8 mmol) is dissolved in 60 ml of anhydrous THF; iodomethane (Aldrich; 2.0 ml; 32.1 mmol) is added dropwise. The reaction mixture is stirred for 24 h at room temperature. The precipitate is filtered off and then rinsed with THF to give 7.03 g of the expected product in the form of the iodide. The filtrate is concentrated to about 10 ml. After 24 h at room temperature, an additional 0.33 g of product is recovered, again in the form of the iodide. The overall yield of these last two steps is 85%.

Physical characteristics:
* m.p.: 136° C. (dec.).
* $^1$H NMR (200 MHz, CDCl$_3$):
7.84 ppm (s; 1H); 4.78 ppm (dd; J=4.32-9.52 Hz; 1H); 4.36 ppm (q; J=7.0 Hz; 2H); 4.25 ppm (q; J=7.0 Hz; H); 3.73 ppm (s; 3H); 3.65 ppm (s; 9H superimposed on m; 1H); 3.32 ppm (dd; J=9.52-14.6 Hz; 1H); 1.38 ppm (t; J=7.0 Hz; 3H); 1.26 ppm (t; J=7.0 Hz; 3H).
* $^{13}$C NMR (50 MHz, CDCl$_3$):
167.50 ppm (s); 166.96 ppm (s); 148.21 ppm (s); 136.06 ppm (s); 135.63 ppm (s); 122.26 ppm (d); 73.93 ppm (d); 5.54 ppm (t; 2CH$_2$); 54.08 ppm (q); 53.85 ppm (q; 3CH$_3$); 26.99 ppm (t); 14.40 ppm (q); 14.23 ppm (q).
* $\alpha_D$ (c=1.0; MeOH)=+34.6.°.

D - Preparation of L-(+)-ergothioneine:

100 ml of hydrochloric acid (SDS; 35%) are added to a mixture of the above trimethylammonium compound (2.05 g; 4.0 mmol) and α-mercaptopropionic acid (Aldrich; 30 g; 283 mmol). The homogeneous solution is refluxed for 26 h by means of an oil bath heated to 110° C. The solvent is evaporated off under vacuum and the residue is taken up with 50 ml of deionized water. The excess β-mercaptopropionic acid is extracted with ethyl ether (3×50 ml). The aqueous solution, whose pH has been brought to 6-7 with a dilute aqueous solution of ammonia, is again evaporated to dryness under vacuum. The residue is purified by chromatography on a silica column with the aid of an elution gradient (AcOEt: 100% then MeOH: 100% and finally MeOH/H$_2$O: 95/5). The desired product is obtained in the form of a white solid (725 mg). This is dissolved in 3 ml of deionized water, and 30 ml of absolute ethanol are then added all at once to this solution. After 24 h at 4° C., the solid is filtered off and then rinsed with absolute ethanol (480 mg). The filtrate is concentrated and the precipitate obtained is recrystallized twice under these same conditions (100 mg) (yield: 55%).

The overall preparative yield of the L-(+)-ergothioneine obtained by this procedure is 19.5%.

Physical characteristics:
, m.p.: 263° C. (dec.).
* $^1$H NMR (200 MHz, D$_2$O):
3.17 ppm (s; 9H superimposed on m; 2H); 3.80 ppm (dd; J=4.5-11.2 Hz; 1H); 6.70 ppm (s; 1H).
* $^{13}$C NMR (50 MHz, D$_2$O):
173.11 ppm (s); 158.82 ppm (s); 126,68 ppm (s); 118.11 ppm (d); 79.82 ppm (d); 54.79 ppm (q); 25.38 ppm (t).
* UV (H$_2$O, c=36.7 μM): $\lambda_{max}$=257 nm.
* $\alpha_D$ (c=1.0; H$_2$O)=+115.6°.

These values are consistent with the information given in the Merck Index, 11th ed. (1989).

EXAMPLE 3: Preparation of L-(+)-ergothioneine:

A - Preparation of L-(+)-2'-mercapto-$N_\alpha,N_\alpha$-dimethylhistidine methyl ester:

An aqueous solution of sodium bicarbonate (Labosi; 3.36 g; 40 mmol) and 20 ml of ethyl ether are added to a solution of the dihydrochloride of L-(+)-$N_\alpha,N_\alpha$-dimethylhistidine methyl ester (1.35 g; 5.0 mmol) in 20 ml of deionized water. Phenyl chlorothionoformate (1.80 ml; 13.0 mmol) is added dropwise at room temperature. The reaction mixture is stirred for 5 h at this same temperature. The aqueous phase is decanted. The organic phase is washed with deionized water (2×50 ml), dried over $MgSO_4$ and evaporated to give an oil, which is taken up with 30 ml of methanol. This solution is treated with triethylamine (Janssen; 2.2 ml; 15.8 mmol) at room temperature for 16 h. The solvent is evaporated off under reduced pressure. The residue is purified by chromatography on a silica column (eluent: AcOEt then AcOEt/MeOH 19/1) to give the desired product. This is recrystallized in the same way as in step A of Example 2 (yield: 76%).

The physicochemical analyses are identical to those of the same compound obtained in step A of Example 2.

Steps B, C and D are carried out in exactly the same way as in Example 2.

The overall preparative yield of the L-(+)-ergothioneine obtained by this procedure is 35.5%.

What is claimed is:

1. A process for the chemical synthesis of the different optical forms of ergothioneine comprising the following successive steps:
   a) providing an $N\alpha$, $N\alpha$-dimethylated histidine ester salt;
   b) reacting the $N\alpha$, $N\alpha$-dimethylated histidine ester salt with a halogenothionoformate, in the presence of a base, thereby obtaining a sulfur-containing substituent in the $N_\alpha$, $N_\alpha$dimethylated histidine ester salt:
   c) protecting the sulfur-containing substituent in the $N\alpha$, $N\alpha$-dimethylated histidine ester salt obtained and converting this protected $N\alpha$, N-dimethylated histidine ester salt to a trimethylammonium $N\alpha$, $N\alpha$-dimethylated histidine ester salt; and
   d) freeing the desired ergothioneine by ester hydrolysis.

2. A process for the chemical synthesis of D, L-ergothioneine comprising the following successive steps:
   a) providing an $N\alpha$, $N\alpha$-dimethylated histidine ester salt;
   b) reacting the $N\alpha$, $N\alpha$-dimethylated histidine ester salt with a halogenothionofromate in the presence of a base to provide a sulfur-containing substituent in the $N\alpha$, $N\alpha$-dimethylated histidine ester salt;
   c) protecting the sulfur-containing substituent in the $N\alpha$, $N\alpha$-dimethylated histidine ester salt in the presence of a base;
   d) reacting the protected sulfur-containing substituent in the $N\alpha$, $N\alpha$-dimethylated histidine ester salt with an alkylating agent; and
   e) freeing the D, L-ergothioneine by saponification.

3. A process for the chemical synthesis of L-(+)ergothioneine comprising the following successive steps:
   a) providing an $N\alpha$, $N\alpha$-dimethylated histidine ester salt;
   b) reacting the $N\alpha$, $N\alpha$-dimethylated histidine ester salt with a halogenothionoformate in the presence of a base to provide a sulfur-containing substituent in the $N\alpha$, $N\alpha$-dimethylated histidine ester salt;
   c) protecting the sulfur-containing substituent in the $N\alpha$, $N\alpha$-dimethylated histidine ester salt in the presence of a base;
   d) reacting the protected sulfur-containing substituent in the $N\alpha$, $N\alpha$-dimethylated histidine ester salt with an alkylating agent; and
   e) freeing the L-(+)-ergothioneine by acid hydrolysis.

4. A process according to claim 3 wherein the above-mentioned acid hydrolysis is carried out in the presence of a mercaptan, to obtain L-(+)-ergothioneine.

5. A process according to claim 4, wherein the mercaptan is selected from the group consisting of an alkylmercaptan and an arylmercaptan.

6. A process according to claim 1 wherein the above-mentioned histidine ester is a $C_1$–$C_6$-alkyl ester.

7. A process according to claim 1 wherein the salt is a halide.

8. A process according to claim 1 wherein the base is selected from the group consisting of a bicarbonate, an amine and an alkylamine.

9. A process according to claim 1 wherein the treatment of the halogenothionoformate with the base is carried out in a polar solvent further comprising two steps, a first step comprising performing the treatment with a weak base having a pKa of less than about 9 in the presence of a polar solvent favoring the solubility of the halogenothionoformate and a second step comprising performing the treatment with a base having a pKa of more than about 10 in the presence of a polar solvent.

10. A process according to claim 3 wherein the saponification is carried out with an amine in a mixture of water and an alcohol.

11. A process according to claim 2 wherein the alkylating agent in step (d) is a methyl halide in an alcohol.

12. A process according to claim 1 wherein the halogenothionoformate is selected from the group consisting of an alkyl halogenothionoformate, an alkenyl halogenothionoformate and an aryl halogenothionoformate.

13. A process according to claim 12, wherein the aryl halogenothionoformate is a phenyl halogenothionoformate.

14. A process according to claim 1, wherein the step of protecting the sulfur-containing substituent in step (c) comprises an acylation.

15. The process of claim 14, wherein the acylation comprises reacting the sulfur-containing substituent with a halogenoformate selected from the group consisting of an alkyl halogenoformate and a phenyl halogenoformate.

16. The process of claim 11, wherein said saponification comprises reacting the compound obtained after step d, with an alkylamine in a water/alcohol mixture.

17. The process of claim 16, wherein said alkylamine is triethylamine and said alcohol is methanol.

18. The process of claim 3, wherein said acid hydrolysis comprises conducting step (e), with a solution of a strong acid in the presence of a large excess of a mercaptan.

19. The process of claim 18, wherein said strong acid is present as a concentrated solution of hydrochloric acid.

20. The process of claim 18, wherein said mercaptan is selected from the group consisting of an alkylmercaptan, an arylmercaptan and β-mercaptopropionic acid.

21. The process of claim 2, wherein the histidine ester is a $C_1$–$C_6$-alkyl ester.

22. The process of claim 3, wherein the histidine ester is $C_1$–$C_6$-alkyl ester.

23. The process of claim 8, wherein said bicarbonate is sodium bicarbonate and said alkylamine is selected from the group consisting of diethylamine and triethylamine.

24. The process of claim 9, wherein said polar solvent favoring the solubility of the halogenothionoformate is an ether and said base having a pKa of more than about 10 is selected from the group consisting of diethylamine and triethylamine.

25. The process of claim 24, wherein said ether is tetrahydrofuran or ethylether.

26. The process of claim 11, wherein said methyl halide is methyl iodide in methanol.

27. The process of claim 1, wherein said ester hydrolysis in step (d) is a saponification.

28. The process of claim 1, wherein said ester hydrolysis in step (d) is an acid hydrolysis.

* * * * *